(12) United States Patent
Gadgil et al.

(10) Patent No.: US 10,918,698 B2
(45) Date of Patent: Feb. 16, 2021

(54) LYOPHILIZED PHARMACEUTICAL COMPOSITION OF FC-PEPTIDE FUSION PROTEIN

(71) Applicant: INTAS PHARMACEUTICALS LTD., Ahmedabad (IN)

(72) Inventors: Himanshu Gadgil, Sanand Ahmedabad (IN); Chandresh Chhatbar, Sanand Ahmedabad (IN); Vijaykant Pandey, Sanand Ahmedabad (IN)

(73) Assignee: INTAS PHARMACEUTICALS LTD., Ahmedabad (IN)

( * ) Notice: Subject to any disclaimer, the term of this patent is extended or adjusted under 35 U.S.C. 154(b) by 622 days.

(21) Appl. No.: 15/300,502

(22) PCT Filed: Mar. 24, 2015

(86) PCT No.: PCT/IB2015/052137
§ 371 (c)(1),
(2) Date: Sep. 29, 2016

(87) PCT Pub. No.: WO2015/150968
PCT Pub. Date: Oct. 8, 2015

(65) Prior Publication Data
US 2017/0112903 A1    Apr. 27, 2017

(30) Foreign Application Priority Data
Mar. 29, 2014 (IN) .......................... 1367/MUM/2014

(51) Int. Cl.
| | | |
|---|---|---|
| *A61K 38/19* | (2006.01) | |
| *A61K 9/19* | (2006.01) | |
| *A61K 47/02* | (2006.01) | |
| *A61K 47/26* | (2006.01) | |
| *A61K 9/16* | (2006.01) | |
| *A61K 47/18* | (2017.01) | |
| *A61K 47/12* | (2006.01) | |
| *C07K 14/52* | (2006.01) | |

(52) U.S. Cl.
CPC .......... *A61K 38/196* (2013.01); *A61K 9/1623* (2013.01); *A61K 9/19* (2013.01); *A61K 47/02* (2013.01); *A61K 47/12* (2013.01); *A61K 47/183* (2013.01); *A61K 47/26* (2013.01); *C07K 14/524* (2013.01); *C07K 2317/21* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,580,856 A | 12/1996 | Prestrelski et al. | |
| 2006/0140934 A1 | 6/2006 | Gegg et al. | |
| 2007/0087005 A1* | 4/2007 | Lazar ................... | C07K 16/303 424/155.1 |
| 2009/0258017 A1* | 10/2009 | Callahan .................. | A61K 9/19 424/134.1 |
| 2010/0278822 A1* | 11/2010 | Fraunhofer ....... | A61K 39/39591 424/133.1 |
| 2011/0123518 A1* | 5/2011 | Pipkin .................. | A61K 9/0078 424/130.1 |

FOREIGN PATENT DOCUMENTS

| | | |
|---|---|---|
| EP | 2468258 | 6/2012 |
| WO | 2013124316 | 8/2013 |
| WO | 2014143770 | 9/2014 |

OTHER PUBLICATIONS

CHMP assessment report for Nplate, p. 1-59. (Year: 2008).*
Nema et al. Pharmaceutical Dosage Forms: Parenteral Medications, Third Edition: vol. 3: Regulations, Validation and the Future, pp. 109-134 (Year: 2010).*
International Search Report for PCT/IB2015/052137, Completed by the Indian Patent Office dated Aug. 9, 2015, 3 Pages.

* cited by examiner

Primary Examiner — Gary B Nickol
Assistant Examiner — Jegatheesan Seharaseyon
(74) Attorney, Agent, or Firm — Brooks Kushman P.C.

(57) ABSTRACT

A novel and thermostable lyophilized pharmaceutical composition of Romiplostim (Fcpeptide fusion protein) along with buffer, bulking agent, stabilizer, and surfactant at pH range of 4.0-6.0.

6 Claims, 4 Drawing Sheets

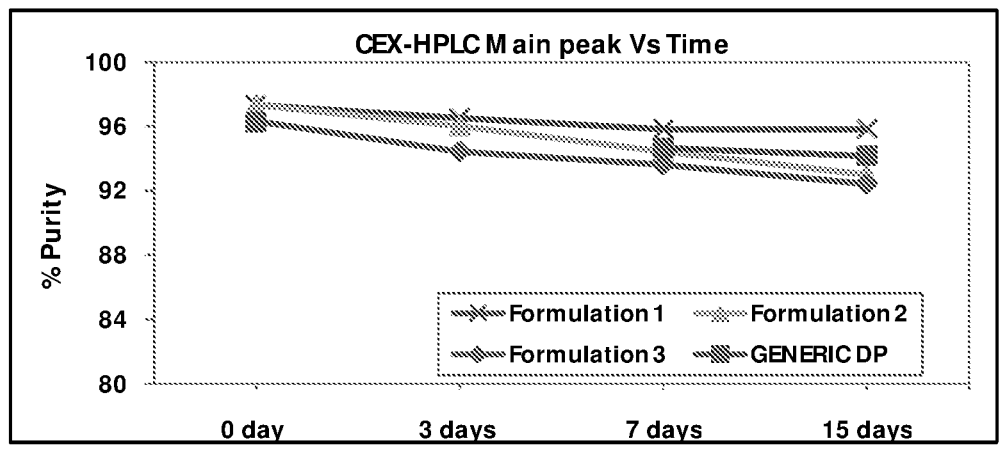
Figure 1: CEX trend analysis of Formulation 1, 2 & 3
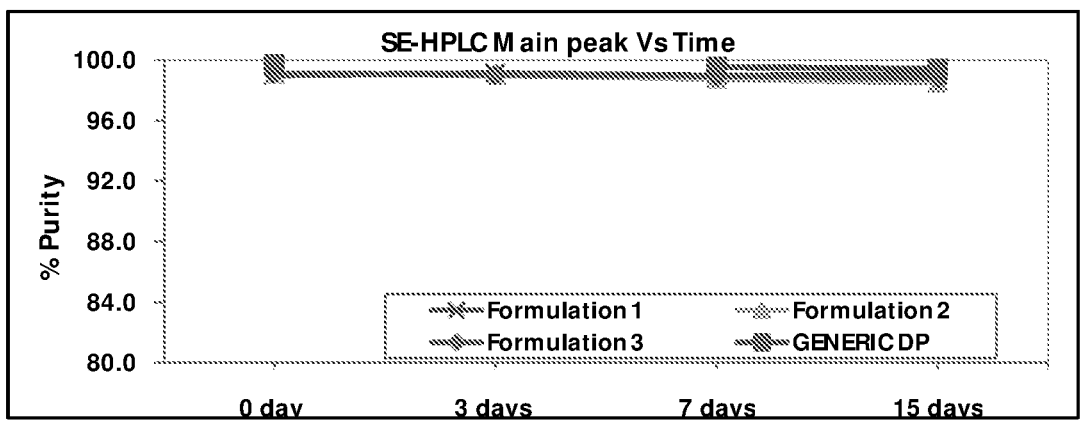
Figure 2: SEC trend analysis of Formulation 1, 2 & 3

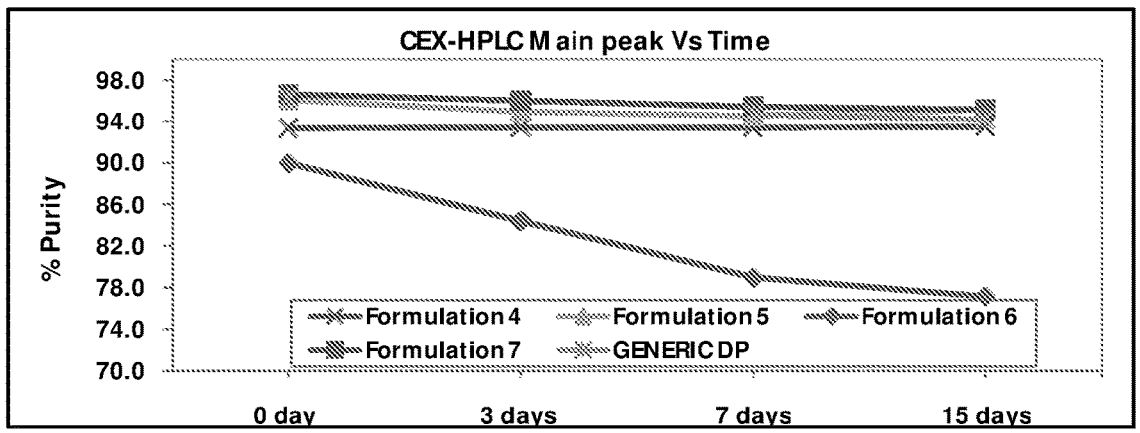
Figure 3: CEX trend analysis of Formulation 4, 5, 6 & 7
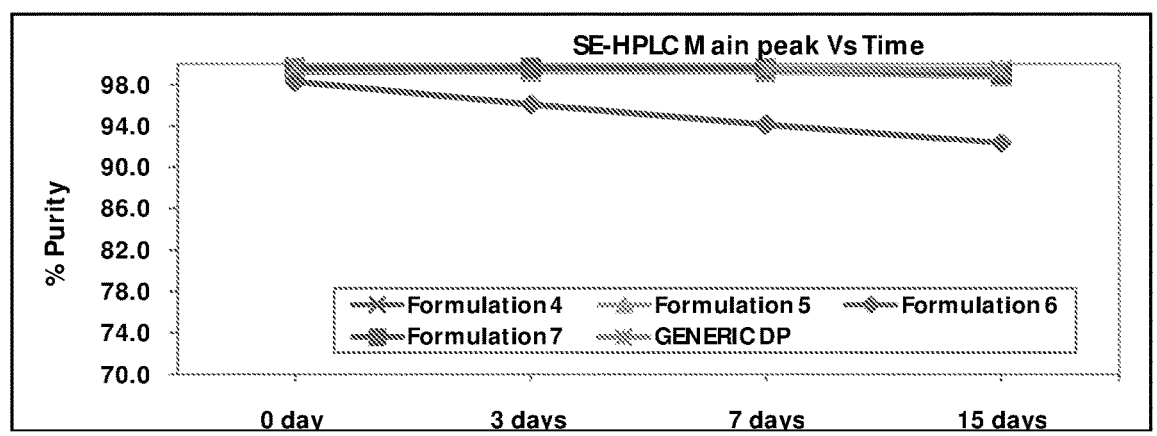
Figure 4: SEC trend analysis of Formulation 4, 5, 6 & 7

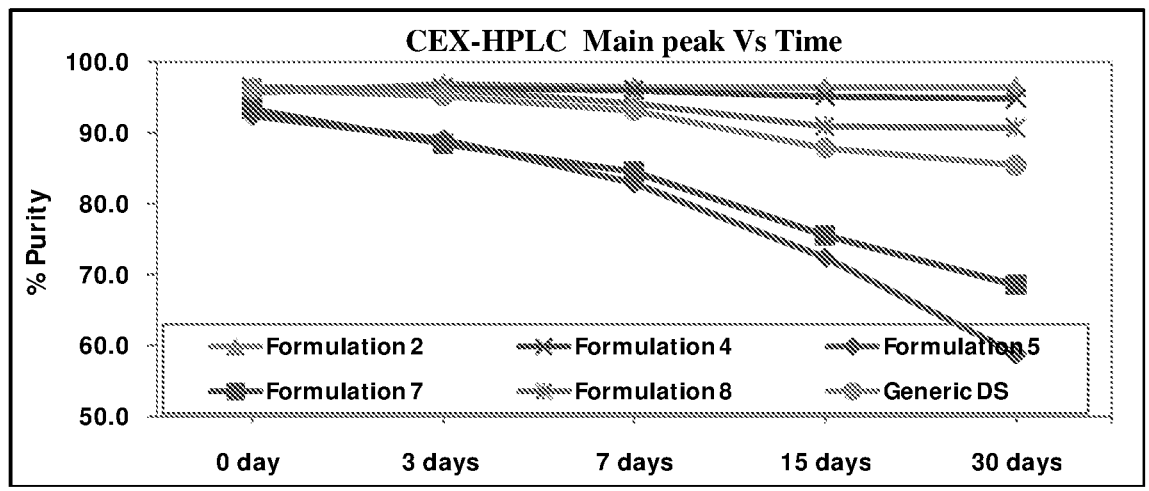
Figure 5: CEX trend analysis of Formulation 2, 4, 5, 7 & 8
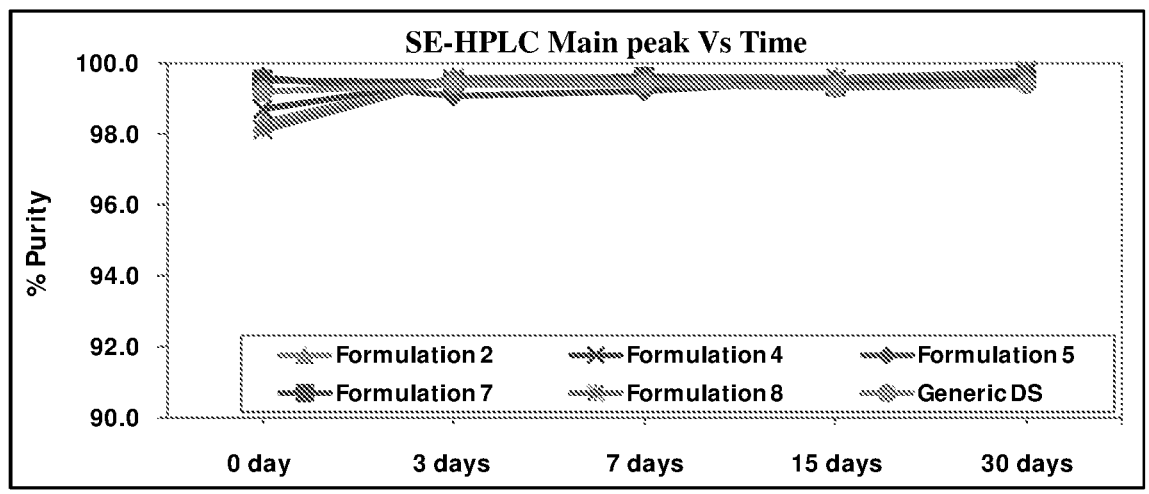
Figure 6: SEC trend analysis of Formulation 2, 4, 5, 7 & 8

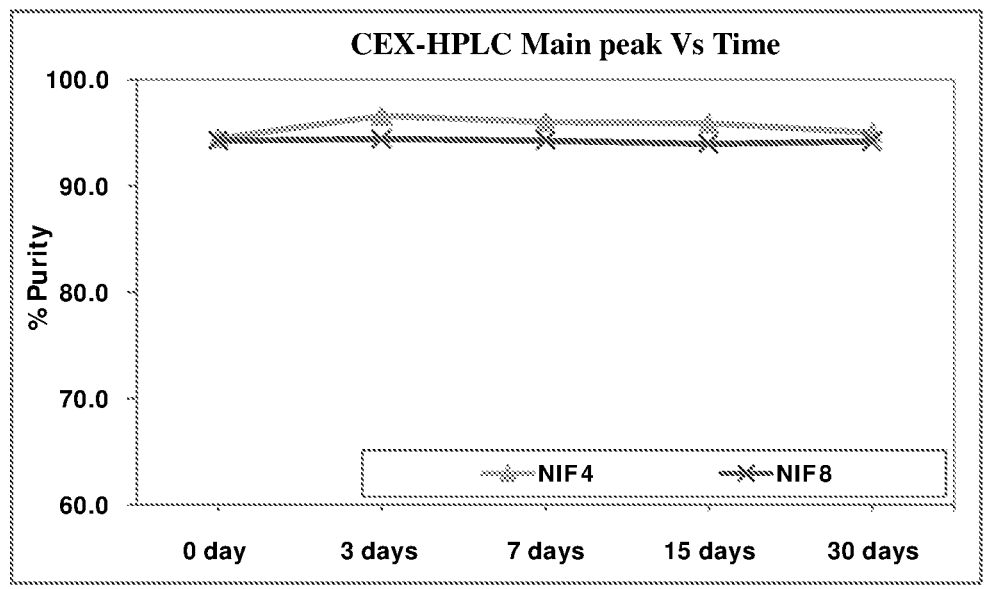
Figure 7: CEX trend analysis of Formulation 4 & 8 charged at 40 °C
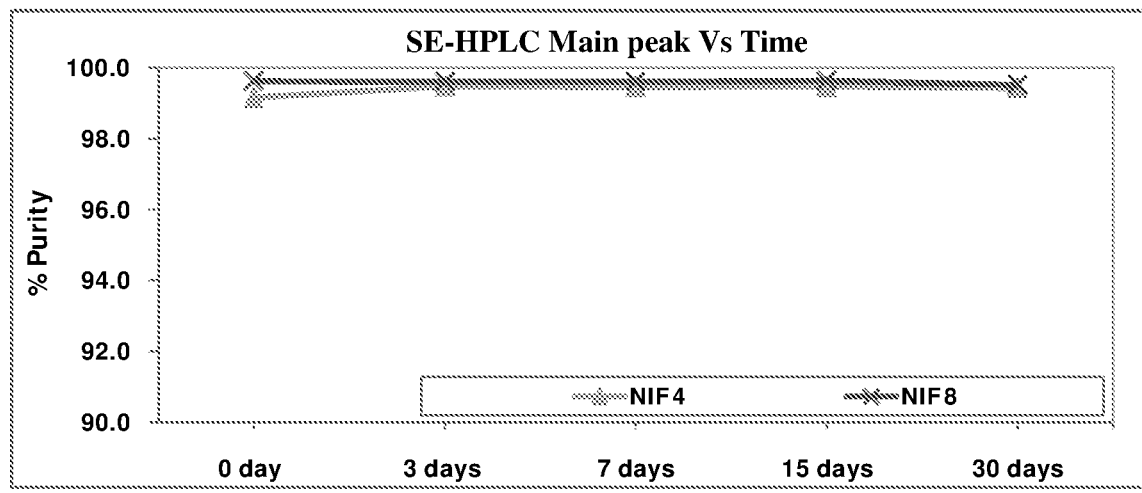
Figure 8: SEC trend analysis of Formulation 4 & 8 charged at 40 °C

LYOPHILIZED PHARMACEUTICAL COMPOSITION OF FC-PEPTIDE FUSION PROTEIN

RELATED APPLICATIONS

Cross-Reference to Related Application

This application is the U.S. national phase of PCT Application No. PCT/IB2015/052137 filed on Mar. 24, 2015, which claims priority to IN Patent Application No. 1367/MUM/2014 filed on Mar. 29, 2014, the disclosures of which are incorporated in their entirety by reference herein.

FIELD OF THE INVENTION

The present invention relates to a lyophilized pharmaceutical composition comprising a Fc-peptide fusion protein, buffer, bulking agent, stabilizer and surfactant.

BACKGROUND OF THE INVENTION

Thrombopoietin (TPO) also known as megakaryocyte growth and development factor (MGDF) is a protein that in humans is encoded by the TPO gene. Thrombopoietin is the physiologically relevant regulator of platelet production.

Thrombopoietin is a glycoprotein hormone produced mainly by the liver and the kidney that regulates the production of platelets by the bone marrow. It stimulates the production and differentiation of megakaryocytes, the bone marrow cells that fragment into large numbers of platelets.

Megakaryocytopoiesis is the cellular development process that leads to platelet production. The protein encoded by this gene is a humoral growth factor necessary for megakaryocyte proliferation and maturation, as well as for thrombopoiesis.

TPO production is regulated by a mechanism different from that for EPO production. There is no "sensor" of the platelet count and no change in the transcription, translation, or release of TPO from its hepatic site of production. Rather, TPO is constitutively produced (reduced only in liver disease), has no storage form, enters the circulation, and is cleared by avid TPO receptors on platelets—and probably to a lesser degree by those on megakaryocytes. When platelet production is reduced, the clearance of TPO is reduced, circulating levels rise, and stimulation of megakaryocyte precursors increases. With increased platelet production, the circulating platelet count rises, more TPO is cleared, and balance is restored.

Romiplostim, marketed as NPLATE® by Amgen Inc., is a member of the TPO mimetic class. It is an Fc-peptide fusion protein (peptibody) that activates intracellular transcriptional pathways leading to increased platelet production via the TPO receptor (also known as cMpl). Romiplostim is produced by recombinant DNA technology in *Escherichia coli* (*E coli*). The peptibody molecule contains two identical single-chain subunits, each consisting of human immunoglobulin IgG1 Fc domain, covalently linked at the C-terminus to a peptide containing two thrombopoietin receptor-binding domains. Romiplostim has no amino acid sequence homology to endogenous TPO. Romiplostim is indicated for the treatment of thrombocytopenia in patients with chronic immune thrombocytopenia (ITP) who has had an insufficient response to corticosteroids, immunoglobulins or splenectomy.

The term "Fc-peptide fusion protein" (peptibody) refers to a molecule comprising peptide(s) fused either directly or indirectly to other molecules such as an Fc domain of an antibody, where the peptide moiety specifically binds to a desired target. The peptide(s) may be fused to either an Fc region or inserted into an Fc-Loop, a modified Fc molecule. Fc-Loops are described in U.S. Patent Application Publication No. US2006/0140934.

Generally, proteins have a very short half-life, and undergo denaturation (such as aggregation, dissociation, and adsorption on the surface of vessels) upon exposure to various factors such as unfavorable temperatures, water-air interface, high-pressure, physical/mechanical stress, organic solvents and microbial contamination. Consequently, the denatured protein loses intrinsic physicochemical properties and physiological activity. Denaturation of proteins is often irreversible, and therefore proteins, once denatured, may not recover their native properties to the initial state.

To overcome the stability problem of proteins in aqueous formulations, therapeutic protein products are made more stable via lyophilization (freeze-drying). Lyophilized products are usually accompanied by sterile aqueous media for reconstitution. After reconstitution, the formulations typically have short useful storage lives, even when stored at low temperatures (e.g., 5° C.).

Typical practices to improve polypeptide stability can be addressed by varying the concentration of elements with the formulation, or by adding excipients to modify the formulation.

US5550856 discloses the stabilization of dried proteins against loss of biological activity in the formulations by adding a reconstitution stabilizer upon rehydration of the dried protein. A kit for producing a formulation by dissolving the dried composition in a solvent containing the reconstitution stabilizer is also described.

US20090258017 discloses a lyophilized therapeutic peptibody compositions comprising a buffer, bulking agent, a stabilizing agent and optionally a surfactant and a kit for preparing an aqueous pharmaceutical composition comprising a first container having a lyophilized therapeutic peptibody composition and a second container having a physiologically acceptable solvent for the lyophilized composition.

However, the bioavailability of commercially available protein therapeutics such as Romiplostim is limited by their short plasma half-life and susceptibility to protease degradation. These shortcomings prevent them from attaining maximum clinical potency.

Hence, there is a need for a stable lyophilized pharmaceutical formulation with an extended shelf life, comprising an Fc-peptide fusion protein which is suitable for therapeutic use to inhibit or counteract reduced platelet production. There is also a need for a stable lyophilized pharmaceutical formulation with an extended shelf life, comprising an Fc-peptide fusion protein suitable for therapeutic use which is easily administered and contains a high protein concentration.

OBJECT OF THE INVENTION

The main object of the present invention is to provide a novel & stable lyophilized pharmaceutical composition of a Fc-peptide fusion protein along with pharmaceutically acceptable carriers.

Another object of the present invention is to provide a novel & stable lyophilized pharmaceutical composition comprising Romiplostim (Fc-peptide fusion protein), buffer, bulking agent, stabilizer, surfactant and pH range of 4.0-6.0.

Yet another object of the present invention is to provide a novel & stable lyophilized pharmaceutical composition of a Fc-peptide fusion protein comprising a buffer system selected from the group consisting of citrate, citro-phosphate, alanine, glycine, arginine, acetate, succinate, histidine either alone or a combination thereof.

Yet another object of the present invention is to provide a novel & stable lyophilized pharmaceutical composition of a Fc-peptide fusion protein comprising bulking agent selected from the group consisting of trehalose, mannitol, glycine, sucrose, dextran, polyvinylpyrolidone, carboxymethylcellulose, lactose, sorbitol or xylitol.

Yet another object of the present invention is to provide a novel & stable lyophilized pharmaceutical composition of a Fc-peptide fusion protein comprising stabilizer selected from the group consisting of monosaccharide such as glucose and mannose; dissacharides such as sucrose, trehalose, and maltose; sugar alcohols such as mannitol and xylitol, polyols such as glycerol, propylene glycol and polyethylene glycol and the like either alone or in combination thereof.

Yet another object of the present invention is to provide a novel & stable lyophilized pharmaceutical composition of a Fc-peptide fusion protein comprising the ionic surfactant selected from the group consisting of a polysorbate-based non-ionic surfactant and a poloxamer-based non-ionic surfactant or a combination thereof.

Yet another object of the present invention is to provide a novel & stable lyophilized pharmaceutical composition of a Fc-peptide fusion protein wherein the formulation is maintained at a pH of about 4.0 to 6.0, more preferably at pH 4.5 to 5.5, in a buffer system selected from the group consisting of citrate, citro-phosphate, alanine, glycine, arginine, acetate, succinate, histidine either alone or a combination thereof.

Yet another object of the present invention is to provide a novel & stable lyophilized pharmaceutical composition of a Fc-peptide fusion protein which encompasses romiplostim as a Fc-peptide fusion protein comprising citrate, citro-phospahte, alanine, arginine as buffer either alone or in combination thereof, trehalose, mannitol either alone or in combination thereof as bulking agent, optionally use of sucrose, PEG, glycerol as stabilizer either alone or in combination thereof, polysorbate 20 as surfactant and formulation is maintained at pH of about 5.0.

Yet another object of the present invention is to provide a novel & stable lyophilized pharmaceutical composition of romiplostim buffer, bulking agent, stabilizer, surfactant; wherein buffer is at concentration of 5 mM to 25 mM and wherein the pH of the composition is in a range of about 4.0-6.0; wherein bulking agent is at concentration of 5.0% to 15.0%; wherein stabilizer is at concentration of 0.1% to 20% w/v; wherein surfactant is at concentration of 0.004% to 0.4% w/v.

SUMMARY OF THE INVENTION

The main aspect of the present invention is to provide a novel & stable lyophilized pharmaceutical composition of a Fc-peptide fusion protein along with pharmaceutically acceptable carriers.

Another aspect of the present invention is to provide a novel & stable lyophilized pharmaceutical composition comprising Romiplostim (Fc-peptide fusion protein), buffer, bulking agent, stabilizer, and surfactant at a pH range of 4.0-6.0.

Yet another aspect of the present invention is to provide a novel & stable lyophilized pharmaceutical composition of a Fc-peptide fusion protein comprising a buffer system selected from the group consisting of citrate, citro-phosphate, alanine, glycine, arginine, acetate, succinate, histidine either alone or a combination thereof.

Yet another aspect of the present invention is to provide a novel & stable lyophilized pharmaceutical composition of a Fc-peptide fusion protein comprising bulking agent selected from the group consisting of trehalose, mannitol, glycine, sucrose, dextran, polyvinylpyrolidone, carboxymethylcellulose, lactose, sorbitol or xylitol.

Yet another aspect of the present invention is to provide a novel & stable lyophilized pharmaceutical composition of a Fc-peptide fusion protein comprising stabilizer selected from the group consisting of monosaccharide such as glucose and mannose; dissacharides such as sucrose, trehalose, and maltose; sugar alcohols such as mannitol and xylitol, polyols such as glycerol, propylene glycol and polyethylene glycol and the like either alone or in combination thereof.

Yet another aspect of the present invention is to provide a novel & stable lyophilized pharmaceutical composition of a Fc-peptide fusion protein comprising the ionic surfactant selected from the group consisting of a polysorbate-based non-ionic surfactant and a poloxamer-based non-ionic surfactant or a combination thereof.

Yet another aspect of the present invention is to provide a novel & stable lyophilized pharmaceutical composition of a Fc-peptide fusion protein wherein the formulation is maintained at a pH of about 4.0 to 6.0, more preferably at pH 4.5 to 5.5, in a buffer system selected from the group consisting of citrate, citro-phosphate, alanine, glycine, arginine, acetate, succinate, histidine either alone or a combination thereof.

Yet another aspect of the present invention is to provide a novel & stable lyophilized pharmaceutical composition of a Fc-peptide fusion protein which encompasses romiplostim as a Fc-peptide fusion protein comprising citrate, citro-phosphate, alanine, arginine as buffer either alone or in combination thereof, trehalose, mannitol either alone or in combination thereof as bulking agent, optionally use of sucrose, PEG, glycerol as stabilizer either alone or in combination thereof, polysorbate 20 as surfactant and formulation is maintained at pH of about 5.0.

Yet another aspect of the present invention is to provide a novel & stable lyophilized pharmaceutical composition of romiplostim buffer, bulking agent, stabilizer, surfactant; wherein buffer is at concentration of 5 mM to 25 mM and wherein the pH of the composition is in a range of about 4.0-6.0; wherein bulking agent is at concentration of 5.0% to 15.0%; wherein stabilizer is at concentration of 0.1% to 20% w/v; wherein surfactant is at concentration of 0.004% to 0.4% w/v.

BRIEF DESCRIPTION OF DRAWINGS

FIG. 1 shows the comparative CEX-HPLC profile of Romiplostim Formulations 1, 2, 3 (Table-4), & Generic DP at 0 D, 3 D, 7 D & 15 D.

FIG. 2 shows the comparative SEC-HPLC profile of Romiplostim Formulations 1, 2, 3 (Table-5), & Generic DP at 0 D, 3 D, 7 D & 15 D.

FIG. 3 shows the comparative CEX-HPLC profile of Romiplostim Formulations 4, 5, 6, 7 (Table-8), & Generic DP at 0 D, 3 D, 7 D & 15 D.

FIG. 4 shows the comparative SEC-HPLC profile of Romiplostim Formulations 4, 5, 6, 7 (Table-9), & Generic DP at 0 D, 3 D, 7 D & 15 D.

FIG. 5 shows the comparative CEX-HPLC profile of Romiplostim Formulations 2, 4, 5, 7, 8 (Table-11), & Generic DS at 0 D, 3 D, 7 D & 15 D & 21 D.

FIG. 6 shows the comparative SEC-HPLC profile of Romiplostim Formulations 2, 4, 5, 7, 8 (Table-12), & Generic DS at 0 D, 3 D, 7 D & 15 D & 21 D.

FIG. 7 shows the comparative CEX-HPLC profile of Romiplostim Formulations 4, 8 (Table-17) charged at 40° C. on OD, 3 D, 7 D & 15 D & 30 D.

FIG. 8 shows the comparative SEC-HPLC profile of Romiplostim Formulations 4, 8 (Table-18) charged at 40° C. on OD, 3 D, 7 D & 15 D & 30 D.

DESCRIPTION OF THE INVENTION

The present invention relates to a lyophilized pharmaceutical composition comprising a Fc-peptide fusion protein, buffer, bulking agent, stabilizer and surfactant.

The present invention relates to a novel, stable, lyophilized pharmaceutical composition comprising Romiplostim (Fc-peptide fusion protein), buffer, bulking agent, stabilizer, and surfactant at a pH range of 4.0-6.0.

As used herein, "buffer" refers to a buffered solution that resists changes in pH by the action of its acid-base conjugate components. Buffer is used in the present invention to maintain the pH in the range of about 4.0 to 6.0, more preferably in the range of 4.5-5.5 and the buffer is selected from the group consisting of citrate, citro-phosphate, alanine, glycine, arginine, acetate, succinate, histidine either alone or a combination thereof.

In yet another embodiment of the present invention, an aforementioned composition is provided wherein the bulking agent selected from the group consisting of trehalose, mannitol, glycine, sucrose, dextran, polyvinylpyrolidone, carboxymethylcellulose, lactose, sorbitol, or xylitol.

In yet another embodiment of the present invention, stabilizer used is selected from the group consisting of monosaccharide such as glucose and mannose; disaccharides such as sucrose, trehalose, and maltose; sugar alcohols such as mannitol and xylitol, polyols such as glycerol, propylene glycol and polyethylene glycol and the like either alone or in combination thereof.

In yet another embodiment of the present invention, surfactant is used in order to prevent adsorption of Fc-peptide fusion protein on the surface of the vial, ampoule, carpoule, cartridge or syringe. Surfactants lower surface tension of a protein solution, thereby, preventing its adsorption or aggregation on to a hydrophobic surface. Preferred surfactants of the present invention include a polysorbate-based non-ionic surfactant and a poloxamer-based non-ionic surfactant or a combination thereof.

In yet another embodiment of the present invention, a novel, stable, lyophilized pharmaceutical composition of a Fc-peptide fusion protein is provided wherein the formulation is maintained at a pH of about 4.0 to 6.0, more preferably at pH 4.5 to 5.5, in a buffer system selected from the group consisting of citrate, citro-phosphate, alanine, glycine, arginine, acetate, succinate, histidine either alone or a combination thereof.

In yet another embodiment of the present invention, a novel, stable, lyophilized pharmaceutical composition of a Fc-peptide fusion protein is provided which encompasses romiplostim as a Fc-peptide fusion protein comprising citrate, citro-phospahte, alanine, arginine as buffer either alone or in combination thereof, trehalose, mannitol either alone or in combination thereof as bulking agent, optionally use of sucrose, PEG, glycerol as stabilizer either alone or in combination thereof, polysorbate 20 as surfactant and formulation is maintained at pH of about 5.0.

In yet another embodiment, the present invention provides a novel & stable lyophilized pharmaceutical composition of romiplostim buffer, bulking agent, stabilizer, surfactant; wherein buffer is at concentration of 5 mM to 25 mM and wherein the pH of the composition is in a range of about 4.0-6.0; wherein bulking agent is at concentration of 5.0% to 15.0%; wherein stabilizer is at concentration of 0.1% to 20% w/v; wherein surfactant is at concentration of 0.004% to 0.4% w/v.

The novel & thermostable lyophilized pharmaceutical composition of Fc-peptide fusion protein described in the present invention has the following advantages:

1. Involves use of a buffer system selected from the group consisting of citrate, citro-phosphate, alanine, glycine, arginine, acetate, succinate and histidine which maintains the pH of the formulation between 4.0 to 6.0, more preferably between 4.5 to 5.5 and also maintains the purity of the formulation at elevated temperature.
2. Involves use of bulking agent to maintain the stability of composition during and after lyophilization.
3. Involves use of surfactant to prevent adsorption of Fc-peptide fusion protein on container.
4. Optionally use of a stabilizer which provides better stability.
5. The pharmaceutical composition of present invention is maintained at pH between 4.5 to 5.5 which is critical in maintaining the purity and stability of the composition at elevated temperatures during storage.
6. Involves operational simplicity.

The following example illustrate the pharmaceutical compositions described in the present invention and the means of carrying out the invention to obtain a thermostable lyophilized pharmaceutical composition comprising Romiplostim.

Example 1 a) Selection of Buffer

TABLE 1

Formulation composition

| Components | Ingredient | F1 | F2 | F3 | F4 | F5 | F6 | F7 | F8 | Generic formulation |
|---|---|---|---|---|---|---|---|---|---|---|
| Active Protein | Romiplostim DS | 0.50 mg/mL | 0.50 mg/mL | 0.50 mg/mL | 0.50 mg/mL | 0.50 mg/mL | 0.50 mg/mL | 0.50 mg/mL | 0.50 mg/mL | 0.50 mg/mL |
| Buffer | L-Histidine | — | — | — | — | — | — | — | — | 10.3 mM |
| | Na-Citrate dihydrate | 10 mM | 10 mM | — | 2.2 mM | — | — | 10 mM | 2.2 mM | — |

TABLE 1-continued

Formulation composition

| Components | Ingredient | F1 | F2 | F3 | F4 | F5 | F6 | F7 | F8 | Generic formulation |
|---|---|---|---|---|---|---|---|---|---|---|
| | Glycine | — | — | 10 mM | — | — | — | — | — | — |
| | Monobasic sodium phosphate dihydrate | — | — | — | 2.5 mM | — | — | — | 2.5 mM | — |
| | dibasic sodium phosphate dihydrate | — | — | — | 2.5 mM | — | — | — | 2.5 mM | — |
| | Citrate monohydrate | — | — | — | 2.8 mM | — | — | — | 2.8 mM | — |
| | L-Arginine | — | — | — | — | 15 mM | — | — | — | — |
| | Alanine | — | — | — | — | — | 15 mM | — | — | — |
| Bulking Agent | Trehalose dihydrate | 10% | — | — | 8% | 8% | 6% | 9% | — | — |
| | Mannitol | — | 4% | 4% | — | — | — | — | — | 4% |
| | Sucrose | — | 2% | 2% | 2% | 2% | 2% | — | 9% | 2% |
| Cryoprotectant/Stabilizer | PEG | — | — | — | — | — | 4% | — | — | — |
| Nonionic surfactant | Polysorbate 20 | 0.004% | 0.004% | 0.004% | 0.004% | 0.004% | 0.004% | 0.004% | 0.004% | 0.004% |
| Vehicle | Water for injection | q.s. to 1 mL | q.s. to 1 mL | q.s. to 1 mL | q.s. to 1 mL | q.s. to 1 mL | q.s. to 1 mL | q.s. to 1 mL | q.s. to 1 mL | q.s. to 1 mL |
| pH modifier | 10% w/v citrate monohydyate | q.s. to pH 5.0 | q.s. to pH 5.0 | — | — | — | — | q.s. to pH 5.0 | — | — |
| | 10% v/v HCl | — | — | q.s. to pH 5.0 | — | q.s. to pH 5.0 | q.s. to pH 5.0 | — | — | q.s. to pH 5.0 |

Method of Preparation:

Romiplostim formulation was prepared in formulation composition given in the above table by dissolving the excipients in water for injection. The protein concentration was set to 0.5 mg/mL and the pH of the formulation is set to 5.0 similar to the reference formulation. 0.75 mL solution filled in 5 mL USP type 1 vial and half stoppered with bromobutyl rubber stopper. After completion of lyophilization cycle, vials are sealed with flip off seals and stored at 2° C.-8° C. Filled vial were charged at 40° C. for 15 days stress stability study. During stability study following test were done:

TABLE 2

Purpose of the tests

| Tests | Purpose of the tests |
|---|---|
| SE-HPLC | To monitor aggregates (H.M.W. impurities) |
| CEX HPLC | To monitor charge related impurities |
| Potency | To monitor effect on in vitro bioassay |
| pH | To monitor effect on pH |
| Physical appearance | To monitor physical appearance |

Example 2

Stress Stability Data of Formulation 1, 2, 3 (Lyophilized):
a) Physical Appearance:
All the samples were observed to be white to pale yellow lyophilized cake.

b) Physical Appearance after Reconstitution:
All the samples were observed to be clear and colorless till 15 D ST c) pH

TABLE 3 pH of Formulation 1, 2 & 3

| Buffers | pH | |
|---|---|---|
| Time point | 0 D | 15 D |
| Formulation 1 | 5.04 | 5.02 |
| Formulation 2 | 5.07 | 5.04 |
| Formulation 3 | 5.05 | 5.10 |
| Generic DP | 5.11 | 5.13 | d) CEX-HPLC

TABLE 4

CEX data of Formulation 1, 2 & 3
% Purity

| Sample ID | 0 day | 3 days | 7 days | 15 days |
|---|---|---|---|---|
| Formulation 1 | 97.3 | 96.5 | 95.8 | 95.8 |
| Formulation 2 | 97.3 | 96.0 | 94.4 | 93.0 |

TABLE 4-continued

CEX data of Formulation 1, 2 & 3
% Purity

| Sample ID | 0 day | 3 days | 7 days | 15 days |
|---|---|---|---|---|
| Formulation 3 | 96.3 | 94.4 | 93.6 | 92.4 |
| GENERIC DP | 96.3 | ND | 94.6 | 94.2 |

Observation:

Based on 15 days stress data the purity of the formulation 1, 2 and 3 was comparable with the reference formulation (generic DP). (FIG. 1)

e) SEC-HPLC

TABLE 5

SEC data of Formulation 1, 2 & 3
% Purity

| Sample ID | 0 day | 3 days | 7 days | 15 days |
|---|---|---|---|---|
| Formulation 1 | 99.0 | 99.1 | 99.0 | 99.0 |
| Formulation 2 | 99.1 | 99.0 | 98.7 | 98.5 |
| Formulation 3 | 99.1 | 99.1 | 99.0 | 98.8 |
| GENERIC DP | 99.7 | ND | 99.6 | 99.4 |

Observation:

Based on 15 days stress data the purity of the formulation 1, 2 and 3 was comparable with the reference formulation (generic DP). (FIG. 2)

f) Potency

The biological activity of Romiplostim is determined by cell based in-vitro bio-assay. The assay is based on the proliferation of meghkarocytes on UT-7 cell line (acute myeloid leukemia) cell line expressing TPO receptor. Romiplostim specifically proliferate activity of UT-7 cell line in a dose dependent manner

TABLE 6

% Potency data of Formulation 1, 2 & 3
% Purity

| Sample ID | 0 day | 3 days | 7 days | 15 days |
|---|---|---|---|---|
| Formulation 1 | 80 | 91 | 83 | 97 |
| Formulation 2 | 88 | 81 | 104 | 127 |
| Formulation 3 | 95 | 91 | 113 | 165 |
| GENERIC DP | 82 | — | 114 | 135 |

Observation:

There is no change in potency at 40° C. after 15 days as compared to initial in all Formulation.

Example 3 a) Physical Appearance

All the samples were observed to be white to pale yellow lyophilized cake.

b) Physical Appearance after Reconstitution

All the samples were observed to be clear and colorless till 15 D ST c) pH

TABLE 7 pH of Formulation 4, 5, 6 & 7

| Buffers | pH Time point | |
|---|---|---|
| | 0 D | 15 D |
| Formulation 4 | 4.9 | 5.0 |
| Formulation 5 | 5.9 | 6.0 |
| Formulation 6 | 6.0 | 6.0 |
| Formulation 7 | 5.0 | 5.0 |
| Generic DP | 5.1 | 5.1 | d) CEX-HPLC

TABLE 8

CEX data of Formulation 4, 5, 6 & 7
% Purity

| Sample ID | 0 day | 3 days | 7 days | 15 days |
|---|---|---|---|---|
| Formulation 4 | 93.3 | 93.4 | 93.4 | 93.5 |
| Formulation 5 | 96.1 | 95.0 | 94.5 | 95.1 |
| Formulation 6 | 89.9 | 84.4 | 79.0 | 77.2 |
| Formulation 7 | 96.6 | 96.0 | 95.4 | 95.1 |
| GENERIC DP | 96.3 | ND | 94.6 | 94.2 |

Observation:

Based on 15 days stress data the purity of the formulation 4, 5 and 7 was comparable with the reference formulation (generic DP). (FIG. 3)

e) SEC-HPLC

TABLE 9

SEC data of Formulation 4, 5, 6 & 7
% Purity

| Sample ID | 0 day | 3 days | 7 days | 15 days |
|---|---|---|---|---|
| Formulation 4 | 99.3 | 99.3 | 99.2 | 99.1 |
| Formulation 5 | 99.3 | 99.3 | 99.2 | 98.8 |
| Formulation 6 | 98.3 | 96.1 | 94.2 | 92.4 |
| Formulation 7 | 99.6 | 99.6 | 99.5 | 99.0 |
| GENERIC DP | 99.7 | ND | 99.6 | 99.4 |

Observation:

Based on 15 days stress data the purity of the formulation 4, 5 and 7 was comparable with the reference formulation (generic DP). (FIG. 4)

f) Potency

The biological activity of Romiplostim is determined by cell based in-vitro bio-assay. The assay is based on the proliferation of meghkarocytes on UT-7 cell line (acute myeloid leukemia) cell line expressing TPO receptor. Romiplostim specifically proliferate activity of UT-7 cell line in a dose dependent manner

TABLE 10

% Potency data of Formulation 4, 5, 6 & 7
DP % relative potency 15 D ST

| Sample ID | 0 day | 3 days | 7 days | 15 days |
|---|---|---|---|---|
| Formulation 4 | 80.0 | 83.0 | 91.0 | 77.0 |
| Formulation 5 | 106.0 | 111.0 | 118.0 | — |
| Formulation 6 | 91.0 | 85.0 | 93.0 | 86.0 |
| Formulation 7 | 67.0 | 93.0 | 72.0 | 78.0 |
| GENERIC DP | 82 | ND | 114 | 135 |

Observation:
There is no change in potency at 40° C. after 15 days as compared to initial in all formulation.

Example 4

Accelerated Stability Data Formulation 2, 4, 5, 7 & 8 (Liquid State):
a) Physical Appearance
All the samples were observed to be clear and colorless till 21 D AT
b) CEX-HPLC

TABLE 11

CEX data of Formulation 2, 4, 5, 7 & 8
% Purity

| Sample ID | 0 day | 3 days | 7 days | 15 days | 21 days |
|---|---|---|---|---|---|
| Formulation 2 | 95.6 | 96.8 | 96.4 | 96.4 | 96.4 |
| Formulation 4 | 96.0 | 96.3 | 96.0 | 95.1 | 94.8 |
| Formulation 5 | 92.4 | 89.1 | 82.9 | 72.4 | 58.8 |
| Formulation 7 | 93.3 | 88.4 | 84.5 | 75.5 | 68.5 |
| Formulation 8 | 96.4 | 96.1 | 94.2 | 90.9 | 90.7 |
| Generic DS | 96.1 | 95.2 | 93.1 | 87.8 | 85.4 |

Observation:
Based on 21 days stress data the purity of the formulation 4 and 8 was comparable with the reference formulation (generic DS). (FIG. 5)
c) SEC-HPLC

TABLE 12

SEC data of Formulation 2, 4, 5, 7 & 8
% Purity

| Sample ID | 0 day | 3 days | 7 days | 15 days | 21 days |
|---|---|---|---|---|---|
| Formulation 2 | 98.3 | 99.6 | 99.6 | 99.6 | 99.7 |
| Formulation 4 | 98.7 | 99.5 | 99.5 | 99.5 | 99.7 |
| Formulation 5 | 99.6 | 99.1 | 99.2 | 99.5 | 99.5 |
| Formulation 7 | 99.5 | 99.5 | 99.6 | 99.3 | 99.5 |
| Formulation 8 | 98.1 | 99.6 | 99.5 | 99.5 | 99.8 |
| Generic DS | 99.2 | 99.4 | 99.4 | 99.3 | 99.4 |

Observation:
Based on 21 days stress data the purity of the formulation 4 and 8 was comparable with the reference formulation (generic DS). (FIG. 6)
d) Potency
The biological activity of Romiplostim is determined by cell based in-vitro bio-assay. The assay is based on the proliferation of meghkarocytes on UT-7 cell line (acute myeloid leukemia) cell line expressing TPO receptor. Romiplostim specifically proliferate activity of UT-7 cell line in a dose dependent manner

TABLE 13

% Potency data of Formulation 2, 4, 5, 7 & 8
% Relative Potency

| Sample ID | 0 day | 3 days | 7 days | 15 days | 21 days |
|---|---|---|---|---|---|
| Formulation 2 | 100 | 98 | 119 | 111 | 88 |
| Formulation 4 | 103 | 114 | 100 | 103 | 86 |
| Formulation 5 | 89 | 72 | 81 | 70 | 71 |
| Formulation 7 | 87 | 103 | 87 | 78 | 81 |
| Formulation 8 | 118 | 97 | 100 | 109 | 89 |
| Generic DP | 115 | 115 | 118 | 125 | 117 |

Observation:
There is no change in potency at 40° C. after 21 days as compared to initial in all Formulations.

Example 5

Rationale:
Based on the above data, all three buffers show a good buffering capacity, and thermo stability profile. To confirm the results obtained during the initial screening, another set of stability study were carried out with the formulation 4 and 8.

TABLE 14

Study condition and Time points for Formulation 4 & 8

| Sr. No. | Condition | Temperature | Time points |
|---|---|---|---|
| 1 | Stress | 40° C. ± 2° C. | 0 D, 3 D, 7 D, 15 D & 30 D |

Method of Preparation:
Romiplostim formulation was prepared in formulation composition given in the above table by dissolving the excipients in water for injection. The protein concentration was set to 0.5 mg/mL and the pH of the formulation is set to 5.0 similar to the reference formulation. 0.75 mL solution filled in 5 mL USP type 1 vial and half stoppered with bromobutyl rubber stopper. After completion of lyophilization cycle, vials are sealed with flip off seals and stored at 2° C.-8° C. Filled vial were charged at 40° C. for 30 days stress stability study. During stability study following test were done:

TABLE 15

Purpose of the tests

| Tests | Purpose of the tests |
|---|---|
| SE-HPLC | To monitor aggregates (H.M.W. impurities) |
| CEX HPLC | To monitor charge related impurities |
| Potency | To monitor effect on in vitro bioassay |
| pH | To monitor effect on pH |
| Physical appearance | To monitor physical appearance | a) Physical Appearance

All the samples were observed to be white to pale yellow lyophilized cake till 28 D ST.

b) Physical Appearance after Reconstitution

All the samples were observed to be clear and colorless till 28 D ST.

c) pH

TABLE 16 pH data of Formulation 4 & 8

| Buffers | pH Time point | | | | |
|---|---|---|---|---|---|
| | 0 D | 3 D | 7 D | 15 D | 30 D |
| Formulation 4 | 5.0 | 5.0 | 5.0 | 5.0 | 5.0 |
| Formulation 8 | 5.1 | 5.1 | 5.1 | 5.0 | 5.0 | d) CEX-HPLC

TABLE 17

CEX data of Formulation 4 & 8 buffers
% Purity

| Sample ID | 0 day | 3 days | 7 days | 15 days | 30 days |
|---|---|---|---|---|---|
| Formulation 4 | 94.5 | 96.6 | 96.0 | 95.9 | 95.0 |
| Formulation 8 | 94.3 | 94.4 | 94.2 | 93.9 | 94.2 |

Observation:

Formulation 4 & 8 are showing good stability and comparable (figure-7).

e) SEC-HPLC

TABLE 18

SEC data of Formulation 4 & 8 buffers
% Purity

| Sample ID | 0 day | 3 days | 7 days | 15 days | 30 days |
|---|---|---|---|---|---|
| Formulation 4 | 99.2 | 99.5 | 99.5 | 99.5 | 99.4 |
| Formulation 8 | 99.6 | 99.6 | 99.6 | 99.6 | 99.5 |

Observation:

Formulation 4 & 8 are showing good stability and comparable in SEC profile (FIG. 8).

f) Potency

TABLE 19

% Potency data of Formulation 4 & 8 buffers
% relative potency
(By cell based assay)

| Sample ID | 0 day | 3 days | 7 days | 15 days | 30 days |
|---|---|---|---|---|---|
| Formulation 4 | 95 | 82 | 99 | 93 | 103 |
| Formulation 8 | 99 | 93 | 96 | 109 | 106 |

Observation:

There is no change in potency at 40° C. after 30 days as compared to initial in all Formulations.

We claim:

1. A lyophilized pharmaceutical composition comprising Romiplostim, citro-phosphate buffer, Polysorbate 20 as surfactant and bulking agent selected from sucrose, trehalose or a combination thereof.

2. The lyophilized pharmaceutical composition of claim 1, wherein the concentration of Romiplostim is between 0.1 mg/mL to 1.0 mg/mL.

3. The lyophilized pharmaceutical composition of claim 1, wherein the Polysorbate 20 is present in the concentration of 0.001% w/v to 1% w/v.

4. The lyophilized pharmaceutical composition of claim 1, wherein the bulking agent is present in the concentration of 5.0% w/v to 15% w/v.

5. The lyophilized pharmaceutical composition as claimed in claim 1 comprising:
    a) 0.5 mg/mL Romiplostim,
    b) 9 mM-11 mM citro-phosphate buffer,
    c) 8.0% w/v-10% w/v sucrose, and
    d) 0.003% w/v-0.005% w/v Polysorbate 20 at pH 5.0.

6. The lyophilized pharmaceutical composition as claimed in claim 1 comprising:
    a) 0.5 mg/mL Romiplostim,
    b) 9 mM-11 mM citro-phosphate buffer,
    c) 7.0% w/v-9.0% w/v trehalose,
    d) 1.0% w/v-3.0% w/v sucrose, and
    e) 0.003% w/v-0.005% w/v Polysorbate 20 at pH 5.0.

* * * * *